United States Patent
Kluger

(12)
(10) Patent No.: US 6,423,064 B1
(45) Date of Patent: Jul. 23, 2002

(54) ORTHOPAEDIC SCREW VARIABLE ANGLE CONNECTION TO A LONGITUDINAL SUPPORT

(75) Inventor: Patrick Kluger, Erbach (DE)

(73) Assignee: Ulrich GmbH & Co. KG, Ulm (DE)

( * ) Notice: Subject to any disclaimer, the term of this patent is extended or adjusted under 35 U.S.C. 154(b) by 0 days.

(21) Appl. No.: 09/831,972

(22) PCT Filed: May 20, 2000

(86) PCT No.: PCT/DE00/01658
§ 371 (c)(1),
(2), (4) Date: Jun. 7, 2001

(87) PCT Pub. No.: WO01/19266
PCT Pub. Date: May 20, 2000

(30) Foreign Application Priority Data

Sep. 15, 1999 (DE) .......................... 199 44 120

(51) Int. Cl.⁷ .............................................. A61B 17/70
(52) U.S. Cl. .......................................... 606/61; 403/373
(58) Field of Search .............................. 606/60, 61, 72, 606/73; 411/397, 383, 400, 401; 403/338, 344, 373, 374.3

(56) References Cited

U.S. PATENT DOCUMENTS

| | | | |
|---|---|---|---|
| 5,501,684 A | | 3/1996 | Schlapfer |
| 5,505,731 A | * | 4/1996 | Tornier .................... 606/61 |
| 5,569,247 A | * | 10/1996 | Morrison ................. 606/61 |
| 5,613,968 A | * | 3/1997 | Lin ........................... 606/61 |
| 5,662,651 A | | 9/1997 | Tornier |
| 5,725,528 A | * | 3/1998 | Errico et al. ............. 606/61 |
| 5,938,663 A | * | 8/1999 | Petreto .................... 606/61 |

FOREIGN PATENT DOCUMENTS

| | | | |
|---|---|---|---|
| DE | 41 07 480 | 9/1992 | |
| DE | 297 12 697 | 11/1997 | |
| WO | WO-98/55038-a | * 12/1998 | ............... 606/61 |

* cited by examiner

Primary Examiner—Eduardo C. Robert
(74) Attorney, Agent, or Firm—Herbert Dubno; Andrew Wilford

(57) ABSTRACT

The bone screw according to the invention for connection at a variable angle with a support bar for osteosynthesis, in particular a pedicle screw for implants for correcting and stabilizing a spinal column, has a threaded shaft (2) for screwing into a vertebra (3) and with a screw head (4) for fixing to a support bar (13), the screw head (4) being formed as a partial sphere with a frustoconically tapered peg (6) having a threaded bore (5), the tapered peg (6) with its threaded bore (5) extending at an acute angle to a longitudinal axis of the threaded shaft (2). The tapered peg (6) is securable by means of a screw (10) engaging in the threaded bore (5) to a clamping sleeve (11) forming a seat (12) for the support bar (13).

7 Claims, 8 Drawing Sheets

ORTHOPAEDIC SCREW VARIABLE ANGLE CONNECTION TO A LONGITUDINAL SUPPORT

The invention relates to a bone screw for connection at different angles to a longitudinal bar for osteosynthesis, in particular to a pedicle screw for implants for correcting and stabilizing a spinal column, with a threaded shaft for screwing into the bone, in particular into a vertebra, and with a screw head made for securing to a support bar.

Such bone screws are known in the prior art, having in order to set one of a plurality of possible angles a set of teeth formed symmetrical to the pivot axis so that they are very expensive and difficult to manufacture and only allow settings to be made at predetermined angular offsets.

Pedicle screws are known for example from German 4,107,480 that have a threaded shaft and a two-part head that fit together via a dovetail-shaped guide. The screw head is formed by a yoke in which the support bar is fixed after it is slipped into the dove tail and secured by a set screw. Such pedicle screws have shown themselves to be effective in practice; however it would be preferable after screwing the pedicle screw into the body of the vertebra if the position on the support bar and the fitting could be done with fewer parts and operational steps.

It is therefore an object of the invention to provide a bone screw of the above-described type that can be freely adjusted after being fitted to the support bar along the axis of same.

This object is achieved by a bone screw of the above-described type wherein the screw head is formed as a partial sphere with a frustoconically tapered peg having a threaded bore, the tapered peg with its threaded bore extends at an acute angle to a longitudinal axis of the threaded shaft, and the tapered peg is securable by means of a screw engaging in the threaded bore to a clamping sleeve forming a seat for the support bar.

The invention has the advantage that when the screw is loosened the clamping sleeve can be rotated on the peg and the support bar can be slid longitudinally through the seat of the sleeve so that the operator can simply adjust the orientation as well as the relative positions of the bar on the bone. As soon as the desired position with any angular setting is reached, tightening of the screw ends both the angular and longitudinal freedoms of movement. No teeth are needed because the peg has a surface inclined relative to the rotation axis of the screw engaging in the threaded bore so that the load moment of the connection between the clamping sleeve and the bone screw does not have to be borne only by friction or engagement with teeth, but instead is distributed over the entire surface of the peg and is borne by bending stress in the clamping sleeve and in the support bar.

Preferably the tapered peg is surrounded on the partial sphere by a support edge for the clamping sleeve so that there is more than engagement only with the flanks of the tapered peg.

A preferred embodiment of the invention is characterized in that the clamping sleeve is formed by a bendable clip having parallel legs connected together by a spring ring forming the seat and having holes through which the screw engages. This embodiment has the advantage that at different stages of tightening of the screw the pivotability of the clamping sleeve or the axial slidability of the support bar can be limited or blocked.

It has shown itself advantageous when the walls of the holes have the same angle as that of the tapered peg so that there is not only line contact with high pressure, but a larger surface area is available.

When the outer wall of the tapered peg has a circumferential outwardly open recess it is possible that the angle of the clamping sleeve can be changed at least limitedly before tightening the screw.

In order to maximize the surface of the abutment edge, the partial sphere is formed by a half sphere merging with the threaded shaft.

An embodiment of the invention is described more closely with reference to the drawing; therein:

Figure 1:
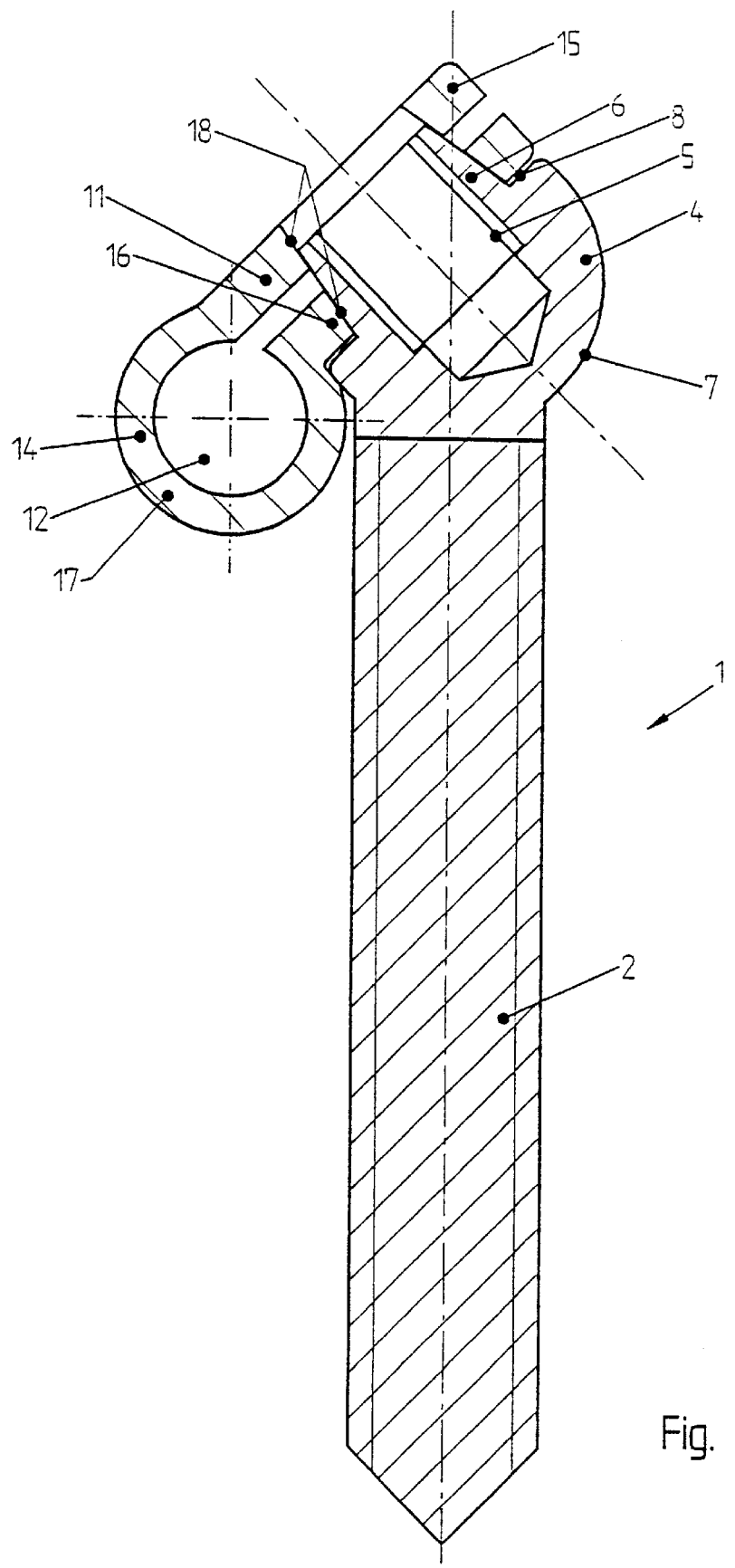
FIG. 1 is an axial section through a bone screw made according to the invention as a pedicle screw with a clamping sleeve mounted on a tapered peg.
Figure 2:
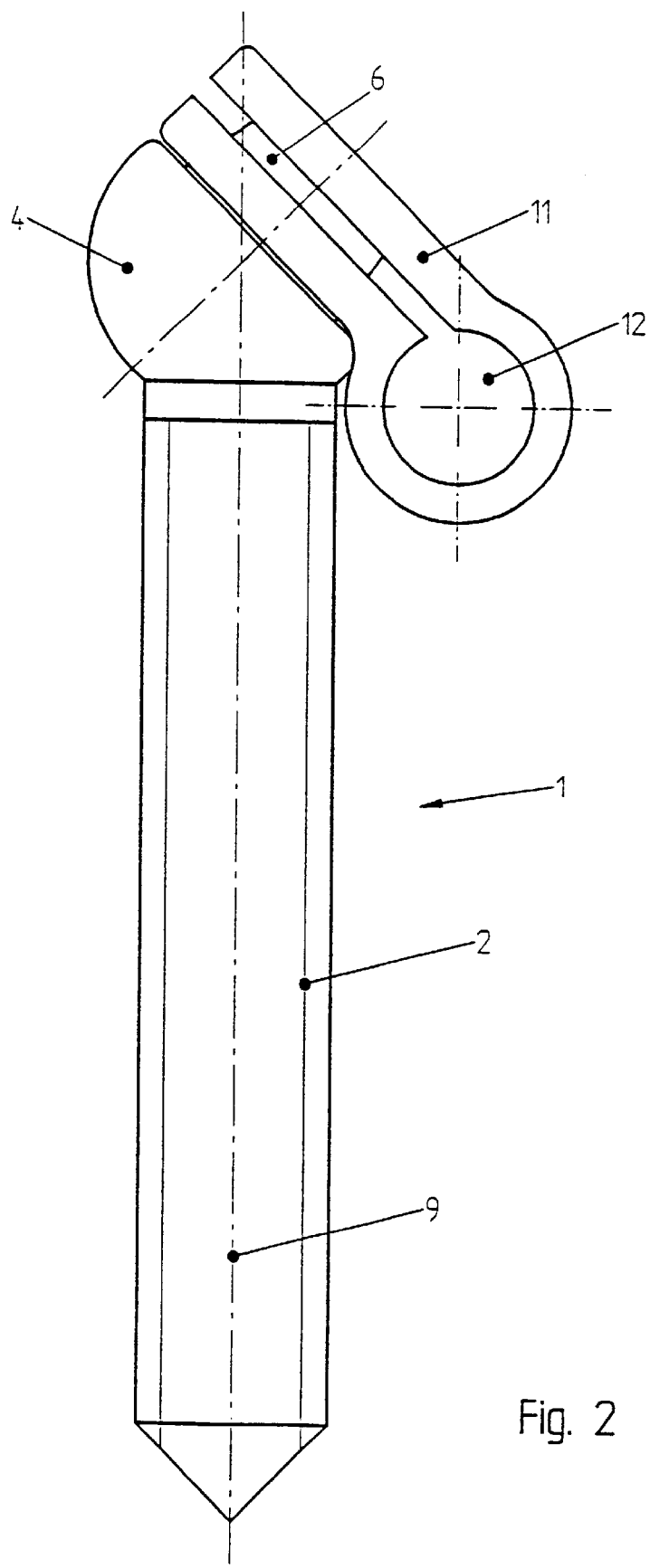
FIG. 2 is a side view of the pedicle screw with the clamping sleeve.
Figure 3:
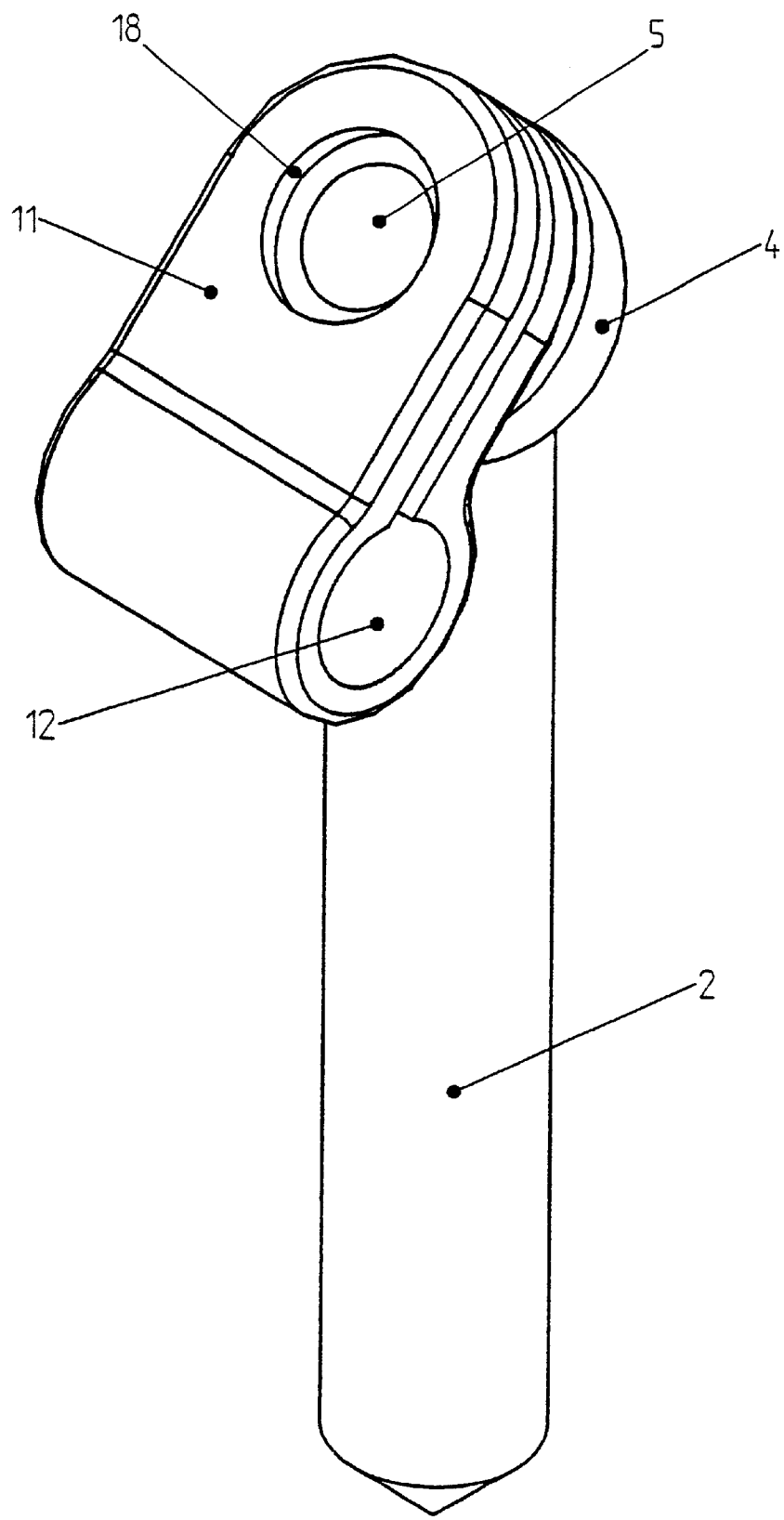
FIG. 3 is a perspective view of the pedicle screw with the clamping sleeve.
Figure 4:
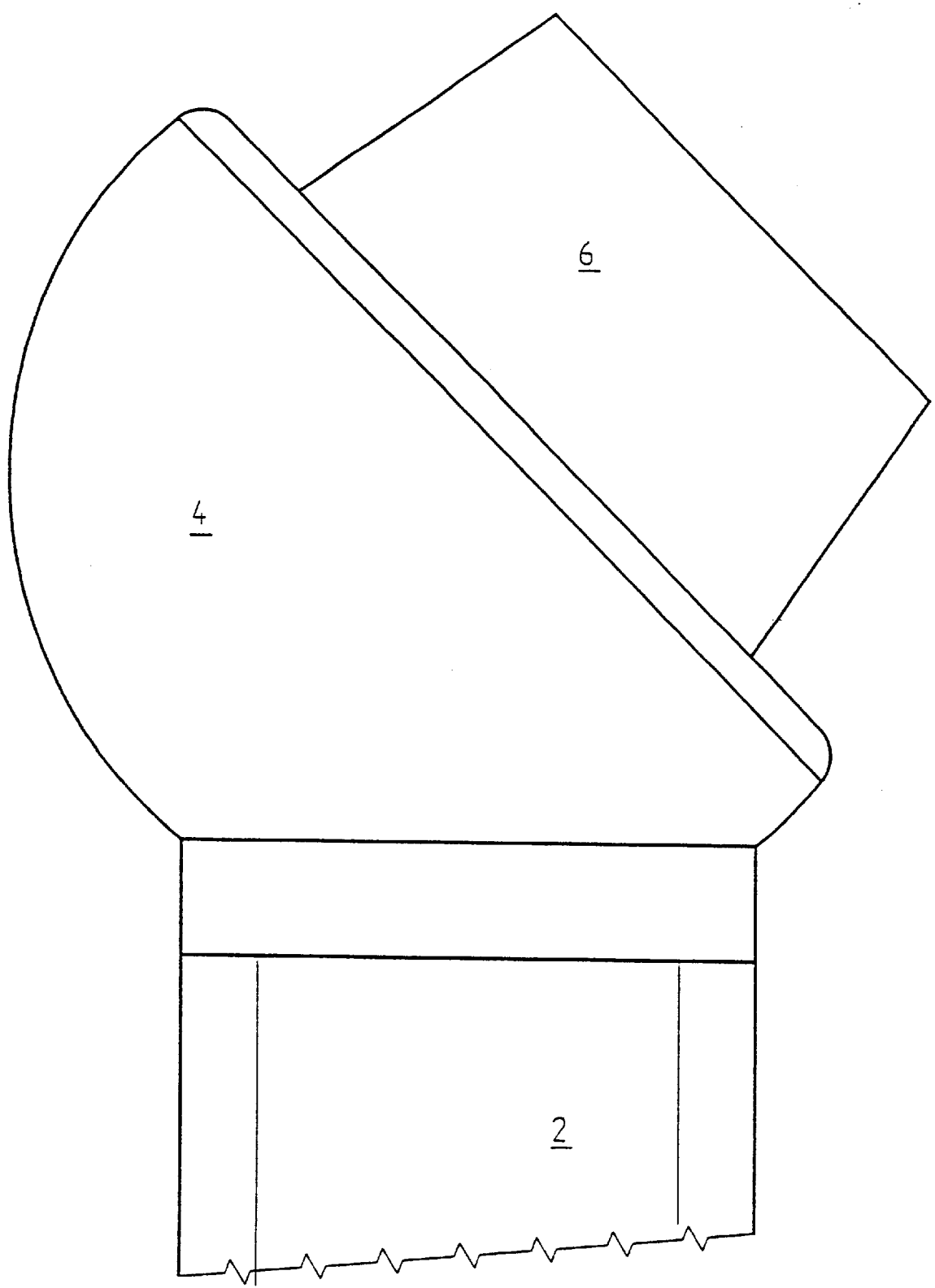
FIG. 4 is a side view of the screw head with the tapered peg and the abutment edge.

The bone screw according to the invention is used in osteosynthesis when an angle-variable connection with a support bar is needed that for example is used in spinal-column surgery in which case the bone screw is called a pedicle screw 1. The pedicle screw 1 shown in the drawing serves for mounting implants used to correct and stabilize the spinal column. The pedicle screw 1 has a threaded shaft 2 that is screwed into a vertebra 3 and a screw head 4 that is formed as a partial sphere with a frustoconically tapered peg 6 having a threaded bore 5, the partial sphere being formed as shown in the drawing as a half sphere 7 whose diameter is such that the tapered pin 6 is surrounded by an abutment edge 6. The tapered pin 6 is set with its threaded bore 5 at an angle to a longitudinal axis 9 of the threaded shaft 2. A clamping sleeve 11 is secured on the tapered peg 6 by a screw 10 engaged in the threaded bore 5 and has a seat 12 shaped for a support bar 13.

Figure 5:
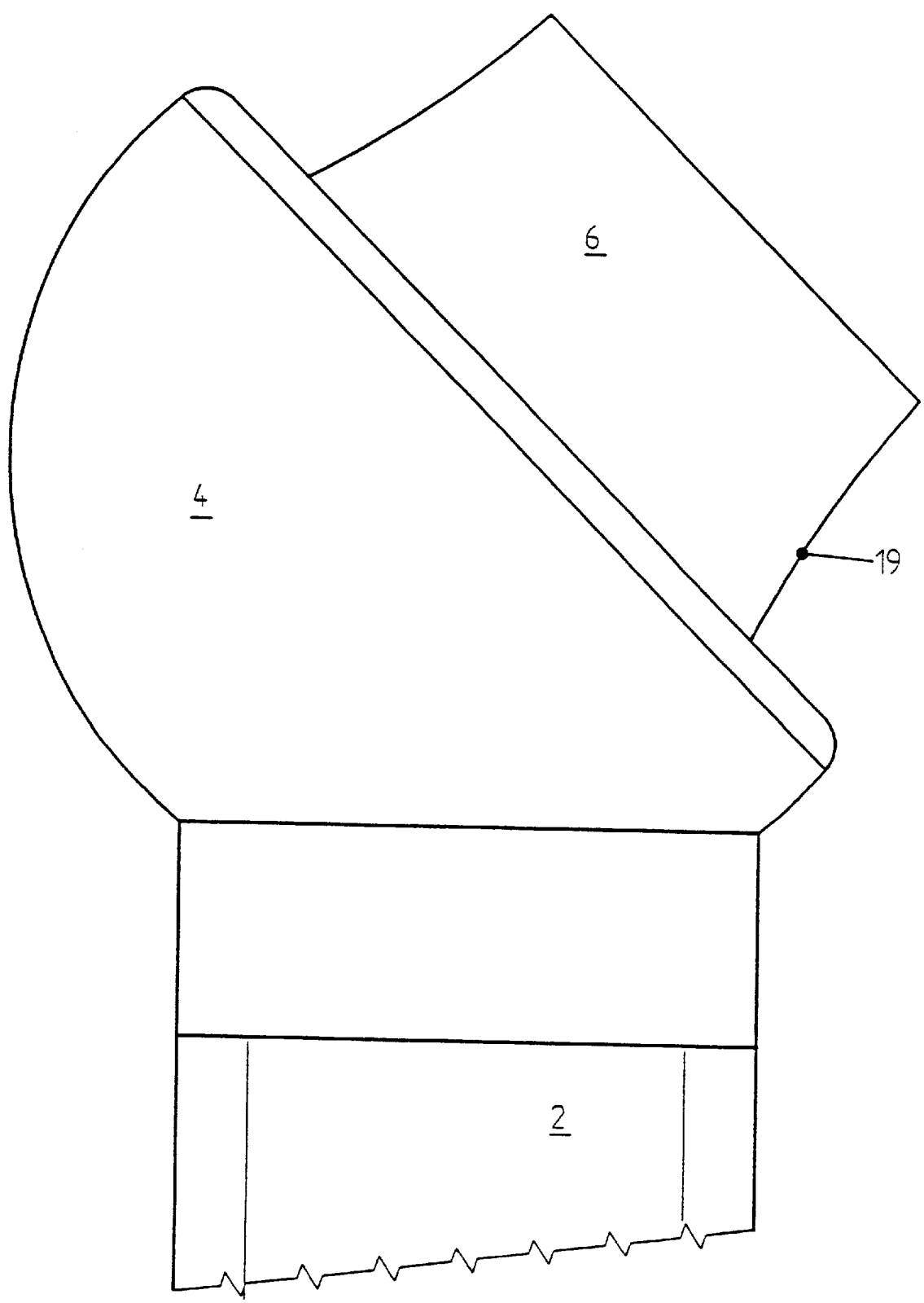
FIG. 5 is a view like FIG. 4 with a recess around the tapered peg.

The clamping sleeve 11 is formed by a clip 14 having parallel legs 15 and 16 connected to a spring ring 17 forming the seat 12 and holes 18 through which the screw 10 engages. The walls of the holes 18 have the same angle as that of the frustoconically tapered peg 6 which can have a concave inset 19 as shown in the embodiment of FIG. 5.

Figure 6:
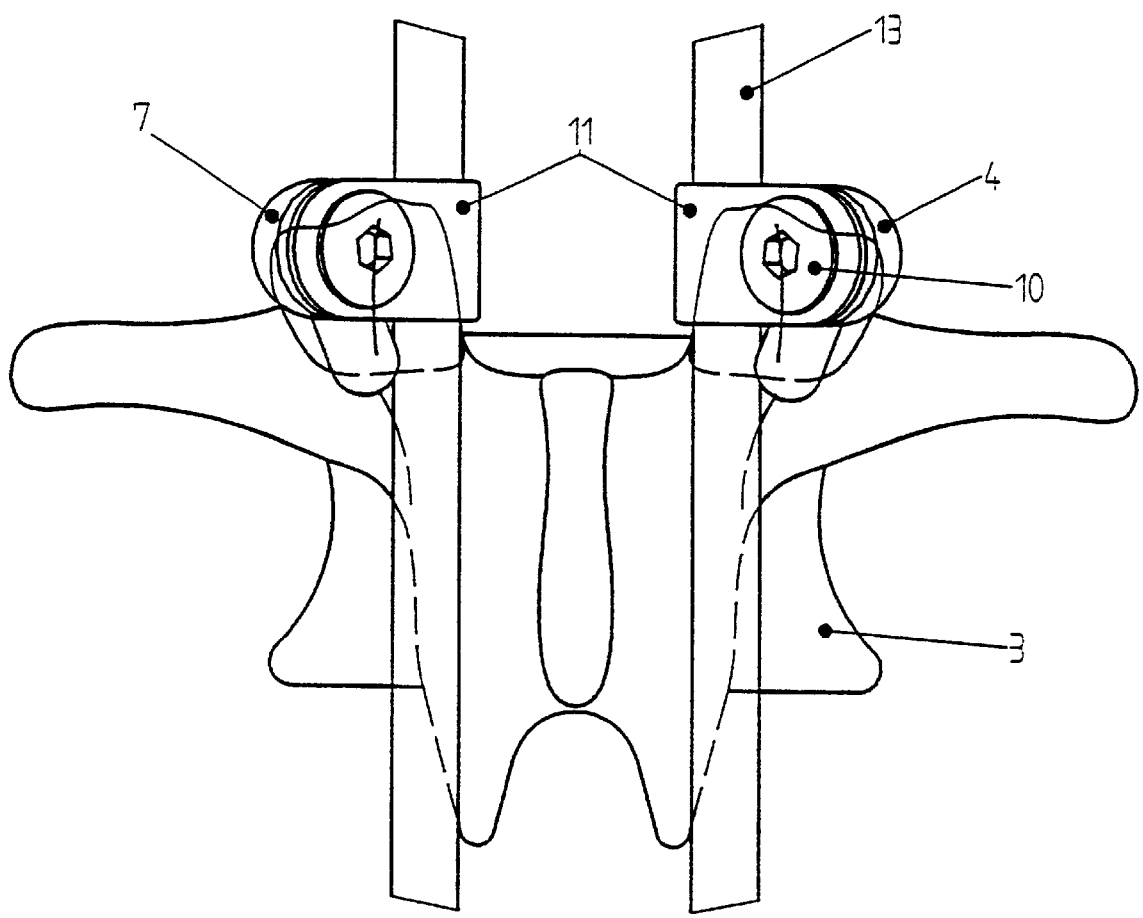
FIG. 6 is a front view of two pedicle screws each on a support bar and screwed into a vertebra.
Figure 7:
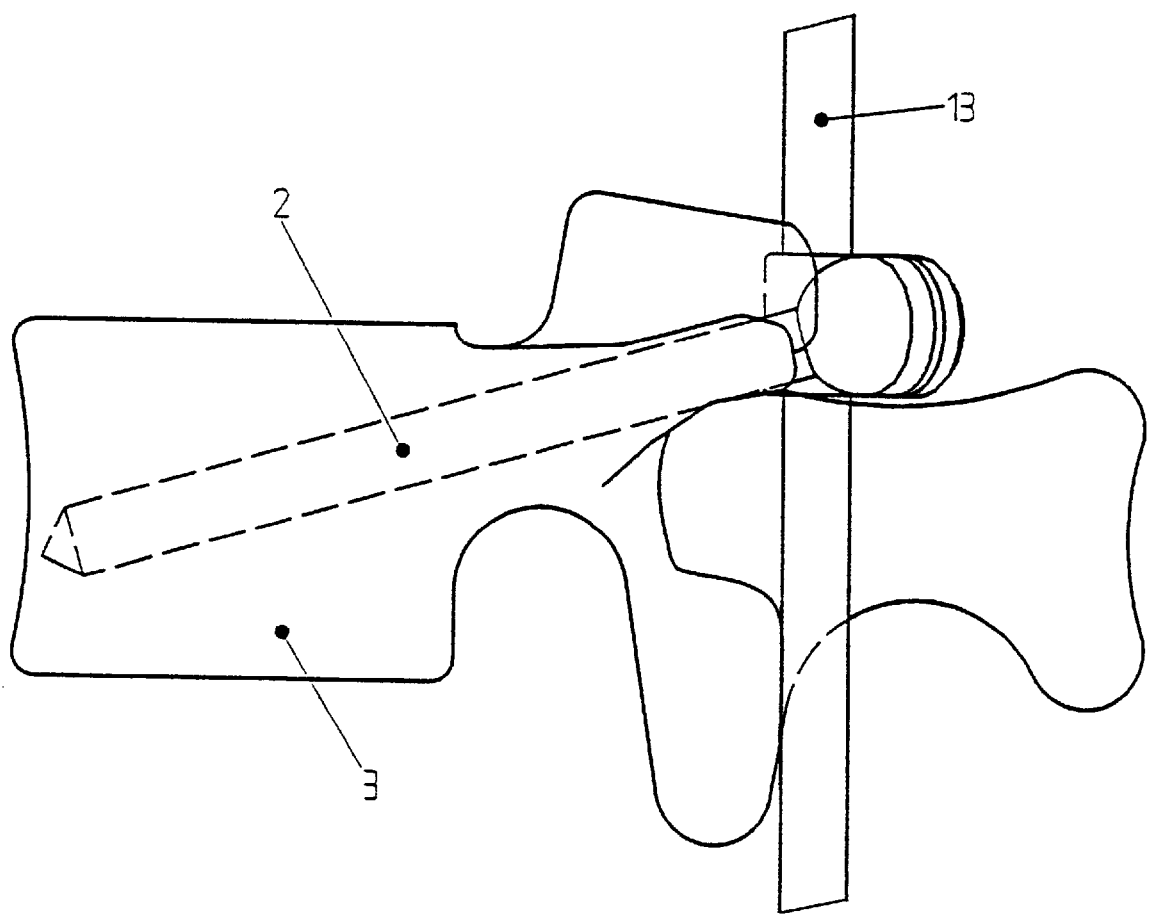
FIG. 7 is a view in the direction of arrow VII of FIG. 6.
Figure 8:
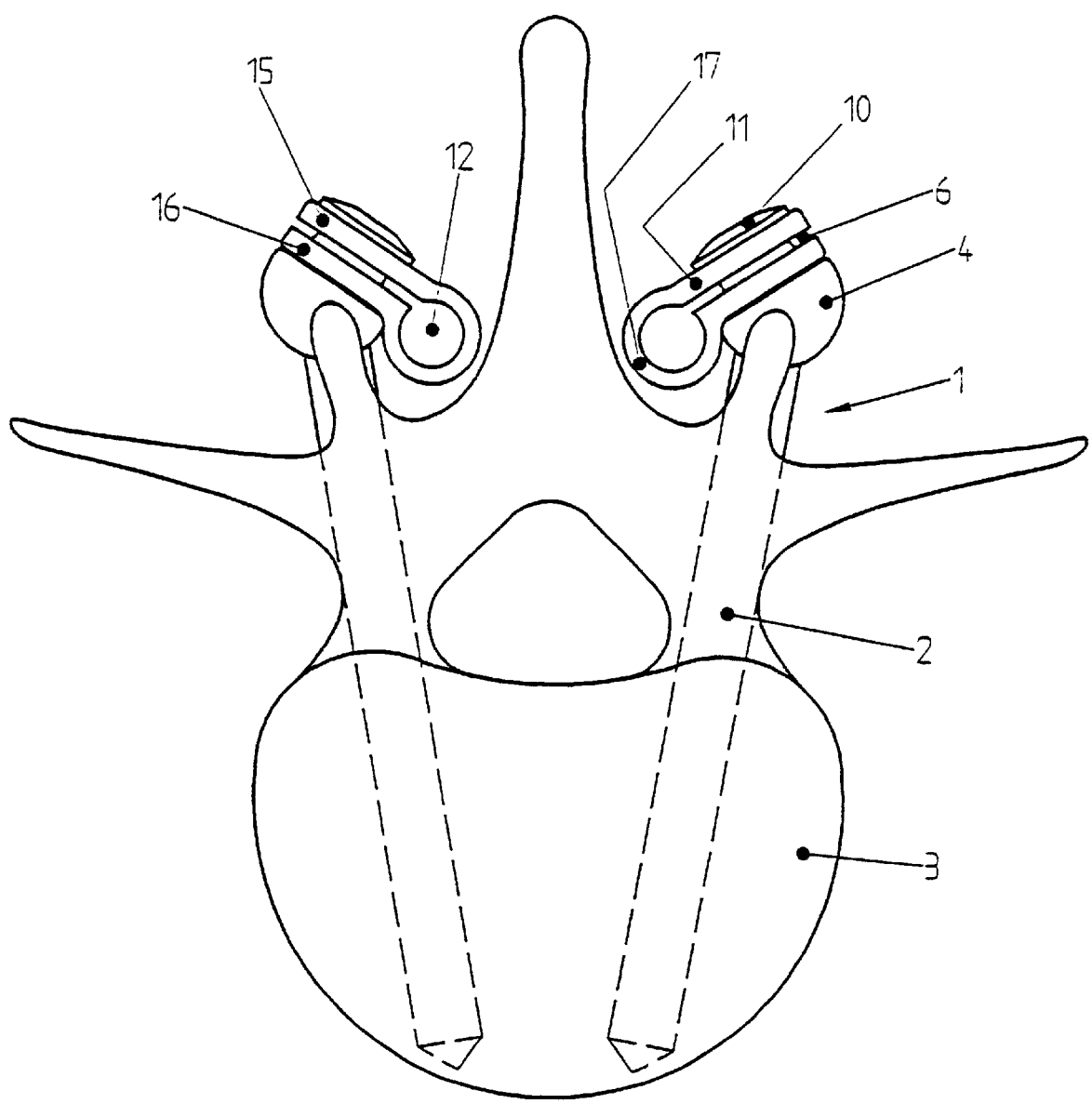
FIG. 8 is a view in the direction of arrow VIII of FIG. 6.

FIGS. 6 and 7 show how the pedicle screw can be used to correct and/or stabilize the spinal column by means of two support bars 13 extending along the spinal column, the shape of the pedicle screw 1 making possible easy manipulation in the operation field since as a result of the angling of the tapered pin 6 there is easy access to set the screw 10 in the threaded bore 5 and it can be set by the operator over a larger angle. When the screw 10 is drawn tight, it simultaneously frictionally clamps the bar 13 in the clamping sleeve 11 at any desired angle and axial position.

What is claimed is:

1. A bone screw comprising:

a threaded shaft extending along a shaft axis and adapted to be screwed into a vertebra;

a head fixed on the shaft and formed with a tapered support peg centered on a peg axis extending at an acute angle to the shaft axis;

a clamping sleeve having a seat shaped to receive a support bar and formed with an opening fittable over the peg; and a retaining screw clamping the sleeve to the head with the peg fitted in the support.

2. The bone screw defined in claim 1 wherein the head forms around the peg a support surface, the screw pressing the sleeve against the surface.

3. The bone screw defined in claim 2 wherein the head is formed as a part sphere centered on a point lying on the shaft axis.

4. The bone screw defined in claim 2 wherein the sleeve is a bendable clip having a pair of legs formed with aligned bored in turn forming the opening.

5. The bone screw defined in claim 4 wherein the legs have a combined thickness greater than a height of the peg above the surface.

6. The bone screw defined in claim 4 wherein the peg and opening are of complementary frustoconical shapes.

7. The bone screw defined in claim 4 wherein the peg has an outwardly concave outer surface.

* * * * *